US00PP32561P2

(12) United States Plant Patent
Hartman

(10) Patent No.: US PP32,561 P2
(45) Date of Patent: Dec. 1, 2020

(54) ***CALADIUM* PLANT NAMED 'CRM OF14-219'**

(50) Latin Name: ***Caladium* X *hortulanum***
Varietal Denomination: CRM OF14-219

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/873,505

(22) Filed: Apr. 23, 2020

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'CRM OF14-219', characterized by its intermediate height and somewhat mounding plant habit; dense and bushy appearance; vigorous growth habit and rapid growth rate; fancy-type leaves that are dark green in color with deep red-colored centers, dark green, white and red-colored blotches and greyed green and white-colored venation; and petioles that are medium green or tannish pink in color with darker-colored stippling, streaks and tessellations.

5 Drawing Sheets

Figure 1:
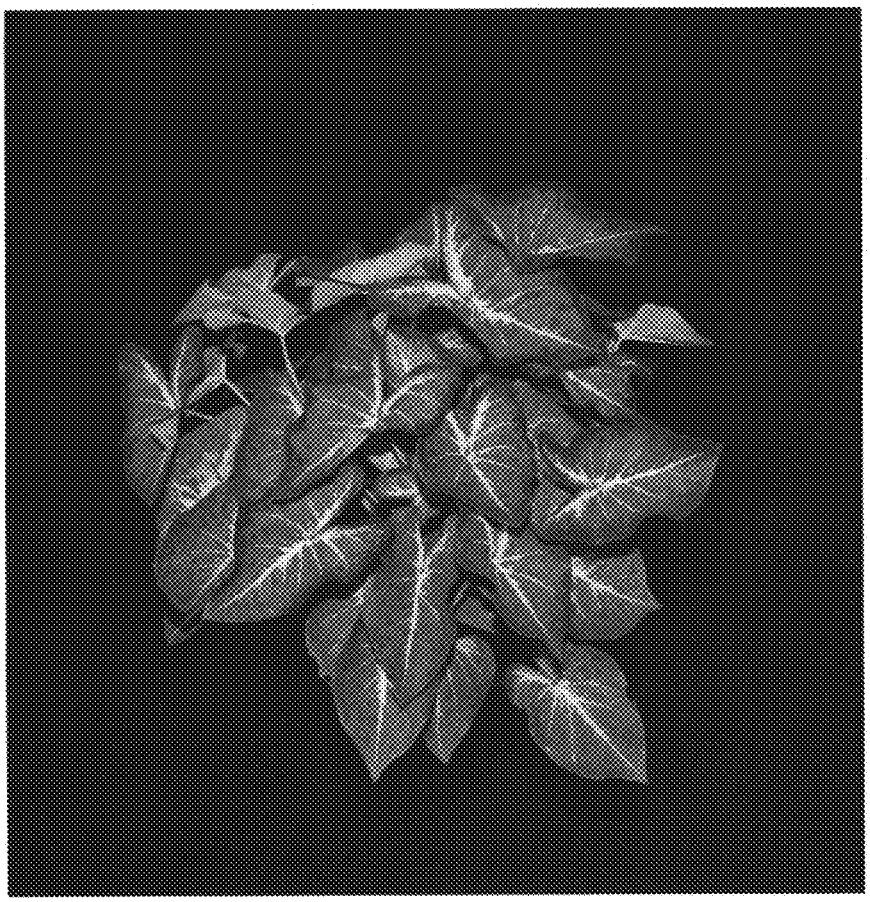

Botanical designation: *Caladium* X *hortulanum*.
Cultivar denomination: 'CRM OF14-219'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'CRM OF14-219'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2013 in Avon Park, Fla. of *Caladium* X *hortulanum* 'Twist 'N Shout', not patented, as the female, or seed, parent with *Caladium* X *hortulanum* 'Water's Edge', disclosed in U.S. Plant Pat. No. 27,965, as the male, or pollen, parent. The new *Caladium* plant was discovered and selected by the Inventor as a single plant within the progeny of the stated cross-pollination in a controlled outdoor nursery environment in Avon Park, Fla. in September, 2014.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2015 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'CRM OF14-219'. These characteristics in combination distinguish 'CRM OF14-219' as a new and distinct *Caladium* plant:

1. Intermediate in height, wider than tall, and somewhat mounding plant habit; dense and bushy appearance.
2. Vigorous growth habit and rapid growth rate.
3. Fancy-type leaves that are dark green in color with deep red-colored centers, dark green, white and red-colored blotches and greyed green and white-colored venation.
4. Petioles that are medium green or tannish pink in color with darker-colored stippling, streaks and tessellations.

Plants of the new *Caladium* differ primarily from plants of the female parent, 'Twist 'N Shout', in the following characteristics:

1. Plants of the new *Caladium* are more mounded than and not as upright as plants of 'Twist 'N Shout'.
2. Leaf bases of plants of the new *Caladium* are sagitate-peltate to cordate in shape whereas leaf bases of plants of 'Twist 'N Shout' are hastate in shape.
3. Plants of the new *Caladium* and 'Twist 'N Shout' differ in leaf color as leaves of the new *Caladium* are dark green in color with deep red-colored centers, dark green, white and red-colored blotches and greyed green and white-colored venation whereas leaves of 'Twist 'N Shout' are olive green in color with green to coppery bronze-colored venation and coppery orange-colored spots and blotches.

Plants of the new *Caladium* differ primarily from plants of the male parent, 'Water's Edge', in the following characteristics:

1. Plants of the new *Caladium* more mounding than and not as upright as plants of 'Water's Edge'.

2. Plants of the new *Caladium* more freely branching than plants of 'Water's Edge'.
3. Plants of the new *Caladium* and 'Water's Edge' differ in leaf color as leaves of the new *Caladium* are dark green in color with deep red-colored centers, dark green, white and red-colored blotches and greyed green and white-colored venation whereas leaves of 'Water's Edge' have bright white-colored venation, grey green-colored interveinal areas surrounded by dark green borders.

Plants of the new *Caladium* can be compared to plants of *Caladium* X *hortulanum* 'Creamsickle', disclosed in U.S. Plant Pat. No. 23,991. In side-by-side comparisons, plants of the new *Caladium* differ primarily from plants of 'Creamsickle' in the following characteristics:

1. Plants of the new *Caladium* and 'Creamsickle' differ in leaf color as leaves of the new *Caladium* are dark green in color with deep red-colored centers, dark green, white and red-colored blotches and greyed green and white-colored venation whereas leaves of 'Creamsickle' have greyed green-colored venation, greyed green and greyed purple-colored interveinal areas interspersed with dark green-colored sectors and borders.
2. Leaves of plants of the new *Caladium* resist fading whereas leaves of plants of 'Creamsickle' fade.

Plants of the new *Caladium* can be compared to plants of *Caladium* X *hortulanum* 'Burning Heart', disclosed in U.S. Plant Pat. No. 27,071. In side-by-side comparisons, plants of the new *Caladium* differ primarily from plants of 'Burning Heart' in the following characteristics:

1. Plants of the new *Caladium* are shorter than and more mounding than plants of 'Burning Heart'.
2. Leaves of plants of the new *Caladium* are smaller than leaves of plants of 'Burning Heart'.
3. Plants of the new *Caladium* and 'Burning Heart' differ in leaf color as leaves of the new *Caladium* are dark green in color with deep red-colored centers, dark green, white and red-colored blotches and greyed green and white-colored venation whereas leaves of 'Burning Heart' are bronze in color with contrasting salmon orange-colored spots.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1 of 7) is a side perspective view of a typical plant of 'CRM OF14-219' in a container and grown in a shade house (tuber de-eyed).

Figure 2:
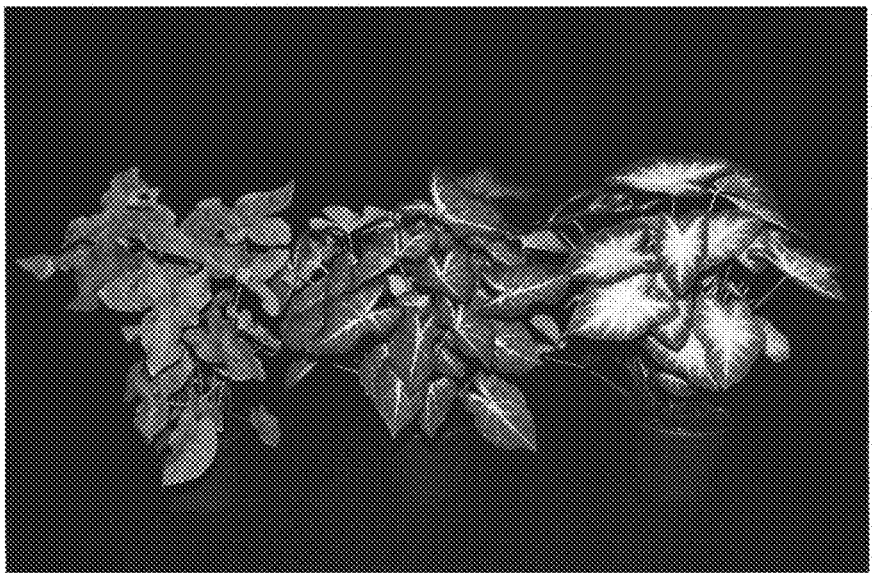

The photograph at the top of the second sheet (FIG. 2 of 7) is a comparison view of typical potted plants of the female parent, 'Twist 'N Shout' (left), 'CRM OF14-219' (center) and the male parent, 'Water's Edge' (right).

Figure 3:
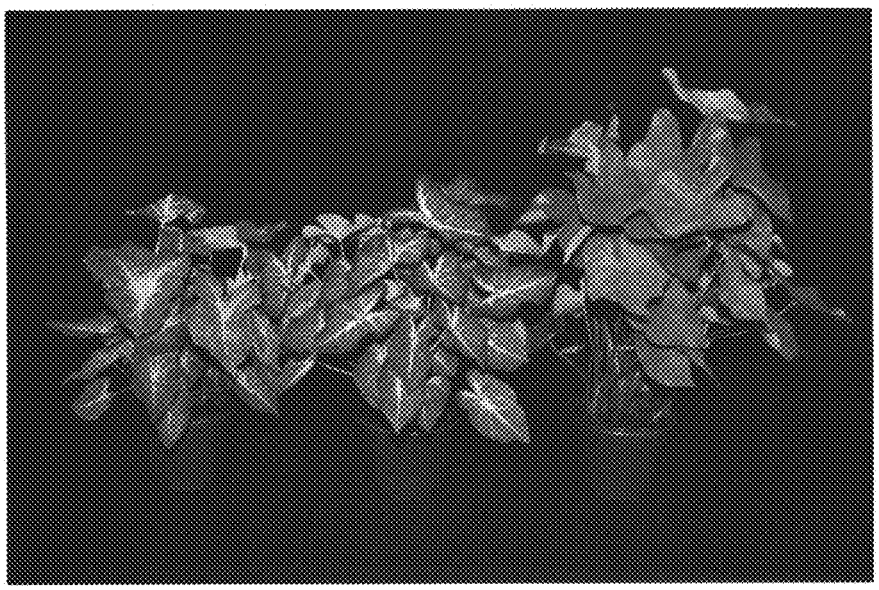

The photograph at the bottom of the second sheet (FIG. 3 of 7) is a comparison view of typical potted plants of 'Creamsickle' (left), 'CRM OF14-219' (center) and 'Burning Heart' (right).

Figure 4:
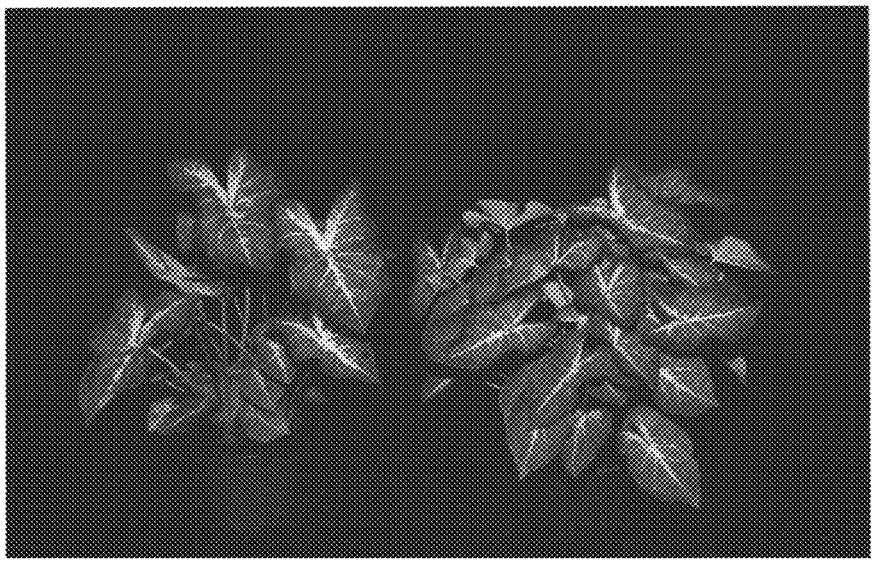

The photograph at the top of the third sheet (FIG. 4 of 7) is a comparison view of typical plants of 'CRM OF14-219' grown in containers, the plant on the left has not had its tuber de-eyed and the plant on the right has had its tuber de-eyed prior to planting.

Figure 5:
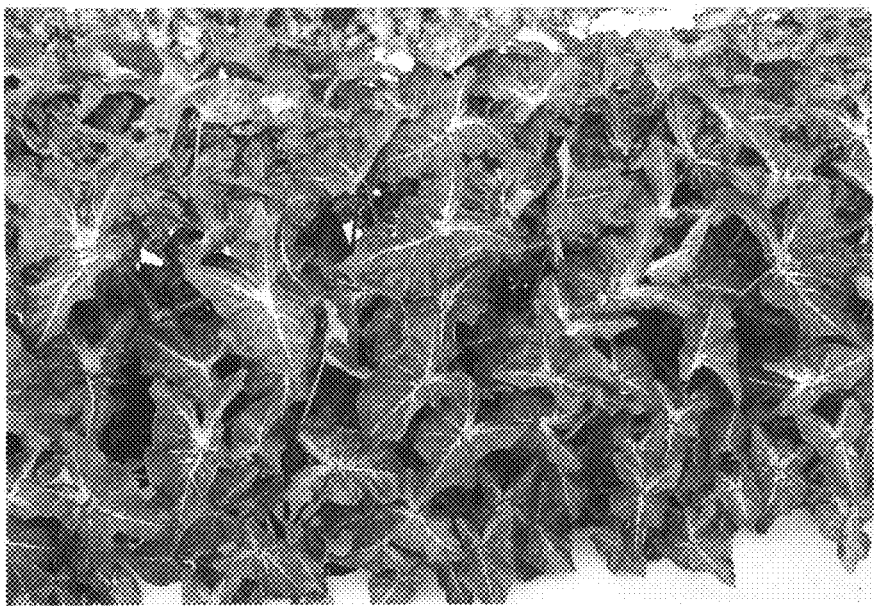

The photograph at the bottom of the third sheet (FIG. 5 of 7) is a side perspective view of typical plants of 'CRM OF14-219' grown in an open production field.

Figure 6:
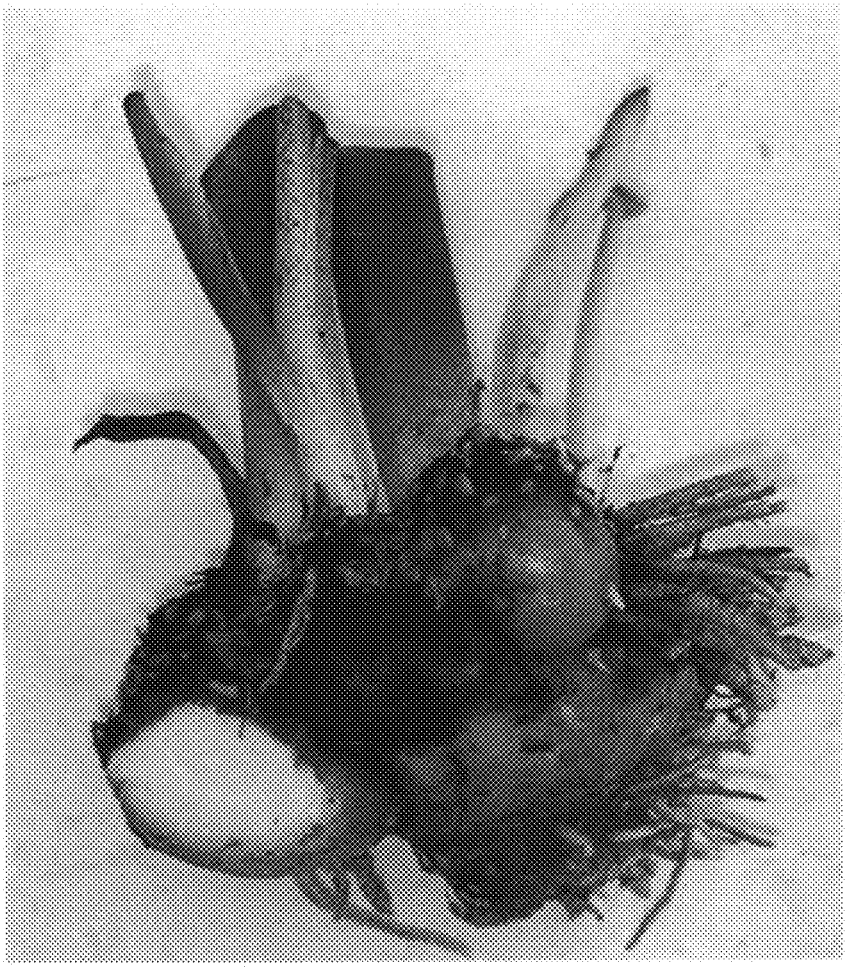

The photograph on the fourth sheet (FIG. 6 of 7) is a close-up view of typical freshly-harvested tubers with roots and leaf petioles of 'CRM OF14-219'.

Figure 7:
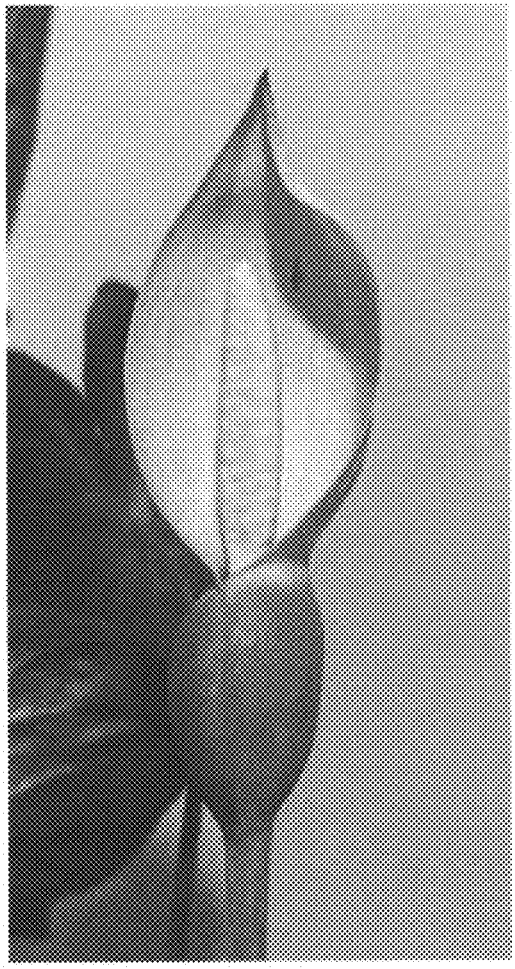

The photograph on the fifth sheet (FIG. 7 of 7) is a close-up view of a typical inflorescence of 'CRM OF14-219'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were eight weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'CRM OF14-219'.

Parentage:

*Female, or seed, parent.*—*Caladium* X *hortulanum* 'Twist 'N Shout', not patented.

*Male, or pollen, parent.*—*Caladium* X *hortulanum* 'Water's Edge', disclosed in U.S. Plant Pat. No. 27,965.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments irregular to ovate to elliptic in shape. Height: About 4.3 cm. Diameter: About 6.3 cm to 7.3 cm. Segment height: About 2.4 cm to 3.8 cm. Segment diameter: About 2 cm to 3.3 cm. Axillary bud shape: Roughly triangular. Axillary bud size: About 3.5 mm by 5 mm. Texture: Thick, starchy; somewhat brittle. Color: Periderm, freshly-harvested: Close to 199B. Periderm, dried: Close to 200A. Epidermis: Close to 179D and N170D. Cortical tissue: Close to 2D; towards the outside, close to 155D. Axillary buds: Close to 38D. Root description: Thick, fleshy contractile roots with few lateral branches; color, close to NN155D. Rooting habit: Medium density.

Plant description:

*Plant type*.—Herbaceous perennial; suitable as a potted plant in containers 15-cm to 25-cm and suitable as a landscape plant in shaded areas.

*Plant and growth habit*.—Intermediate in height, wider than tall, and somewhat mounding plant habit when tubers are de-eyed; dense and bushy appearance; vigorous growth habit and rapid growth rate; potted plants finish in saleable form in about six weeks after planting tubers; leaf petioles and leaves arise from one or more growing points on tubers; leaf petioles initially upright and somewhat outwardly leaning with development.

*Plant height, from soil level to top of foliar plane, shade house-grown potted plants*.—About 31 cm to 36 cm.

*Plant height, from soil level to top of inflorescences, shade house-grown potted plants*.—About 31.5 cm.

*Plant diameter or spread, shade house-grown potted plants*.—About 38.5 cm to 47 cm.

*Number of shoots per plant, shade house-grown potted plants, tubers not de-eyed*.—About three to four develop per #1 tuber.

*Number of shoots per plant, shade house-grown potted plants, tubers de-eyed*.—About 7 to 14 develop per #1 tuber.

*Cataphylls, shade house-grown potted plants*.—Length: About 7.6 cm. Width: About 1.4 cm. Shape: Wedge-shaped. Apex: Acute. Base: Sheathing the stem. Color: With development, color becoming closer to 165B and 200B.

Leaf description:

*Arrangement and type*.—Alternate; simple; fancy-type.

*Length, shade house-grown potted plants, tubers de-eyed*.—About 13 cm to 15.5 cm.

*Length, shade house-grown potted plants, tubers not de-eyed*.—About 14 cm to 21.5 cm.

*Width, shade house-grown potted plants, tubers de-eyed*.—About 7 cm to 9.3 cm; when flattened, about 8 cm to 10 cm.

*Width, shade house-grown potted plants, tubers not de-eyed*.—About 8.5 cm to 12.5 cm; when flattened, about 10 cm to 14 cm.

*Shape*.—Ovate.

*Apex*.—Acute to acuminate.

*Base*.—Sagittate-peltate, cordate.

*Margin*.—Entire; somewhat undulate with broad undulations.

*Texture and luster, upper surface*.—Glabrous, blotches may be recessed; dull sheen.

*Texture and luster, lower surface*.—Glabrous, blotches may be puckered; slightly glaucous with a dull sheen.

*Venation pattern*.—Pinnate.

*Color, shade house-grown potted plants*.—Developing and fully developed leaves, upper surface: Background color: Close to 147A and 146A. Towards the margins: Close to 147A and 146A. Leaf edge: Narrow, close to 187A. Basal notch: Close to 187A and 187B. Leaf attachment point: Close to 187B. Midvein: Close to 196B; surrounded with close to 155B and 155C. Lateral venation: Close to 196B; may be tinged with close to 187A and flecked with 147A and 146A; surrounded with close to 155A and 155B. Interveinal areas: Close to 185A tinged with close to 53A. Blotches and spots: Close to 147A, 146A, NN155A and 180A. Developing and fully developed leaves, lower surface: Background color: Close to 191A tinged with close to 182A and 182B. Towards the margins: Close to 191A. Leaf edge: Close to 187A. Basal notch: Close to 187A. Leaf attachment point: Close to N186C to N186D. Midvein: Close to 155C tinged with close to 164D; surrounded with close to NN155C. Lateral venation: Close to 196B; surrounded with close to NN155C and 155C. Interveinal areas: Close to 187B. Blotches and spots: Close to 187B.

*Petioles*.—Aspect: Initially upright and straight and somewhat outwardly leaning with development; flexible. Length, shade house-grown potted plants: About 19.5 cm to 31.5 cm. Diameter, distally, shade house-grown potted plants: About 3 mm to 5 mm. Diameter, proximally, shade house-grown potted plants: About 5 mm to 7.5 mm. Texture and luster: Smooth, glabrous; glaucous. Color, shade house-grown potted plants: When developing and fully developed: Close to N170D with faint stippling, streaks and tessellations of close to 200A tinged with 147A; or may be close to 147B to 147C and proximally, close to 146C with faint stippling, streaks and tessellations of close to 200A; just below the leaf junction, close to 147D and 165D with faint stippling, streaks and tessellations of close to 200C. Wing length, shade house-grown potted plants: About 6 cm to 9 cm. Wing diameter, shade house-grown potted plants: About 1 cm. Texture and luster, inner and outer surfaces: Smooth, glabrous; dull. Wing color, shade house-grown potted plants: Outer surface: Close to 147D and NN155C with faint stippling, streaks and tessellations of close to 200A. Inner surface: Close to N155D; colors and patterns on the outer surface are visible on the inner surface.

Inflorescence description: Inflorescences observed on eight week-old shade house-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about eight weeks after growth commences; inflorescences last about three days before fading; inflorescences persistent.

*Spathe*.—Length, overall: About 8.5 cm. Length, distal open portion: About 5.5 cm. Length, proximal closed portion: About 3 cm. Width, distal open portion: About 3.5 cm. Depth, distal open portion: About 1.5 cm. Width, at constriction: About 1.4 cm. Width, proximal closed portion: About 1.7 cm. Shape, open portion: Ovate, elliptic. Apex: Acute. Base: Acute. Margin: Entire; smooth. Texture and luster, front surface: Smooth, glabrous; dull. Texture and luster, rear surface: Smooth, glabrous; dull, proximally, glaucous. Color, front surface: Distal open portion: Close to 155D with sparse blotches and specks, close to 181A; with development, color becoming closer to 199B to 199C. Proximal closed portion: Close to 147C, 138C and 139D; towards the base, faintly flushed with close to N186C; color does not change with development. Color, rear surface: Distal open portion: Close to 155C and centers, close to 145C; color becoming closer to 199B to 199C with development. Proximal closed portion: Close to 139C to 139D flushed with close to 147D; color does not change with development.

*Spadix*.—Length, overall: About 6 cm. Length, male flower zone: About 4.8 cm. Length, sterile zone: About 1.4 cm. Length, female flower zone: About 1.2 cm. Diameter, male flower zone: About 7 mm. Diameter, sterile flower zone: About 4 mm. Diameter, female flower zone: About 5 mm. Shape: Columnar, spindle-shaped. Apex: Acute. Base: Obtuse. Aspect: Upright. Color, mature, male zone: Close to 159D. Color, mature, sterile zone: Close to N159D. Color, mature, female zone: Close to 155B, N155C and 36D. Male flowers: Quantity per spadix: About 75. Shape: Obovate. Height: About 2.5 mm. Diameter: About 3 mm. Pollen amount: Moderate. Pollen color: Close to 4C. Female flowers: Quantity per spadix: About 40. Shape: Obovate. Height: About 2.5 mm. Diameter: About 2 mm. Stigma color: Close to 155B. Ovary color: Close to N155C and 36D.

*Scape*.—Length: About 23 cm. Diameter: About 4.5 mm. Strength: Sturdy; flexible. Aspect: Mostly erect. Texture and luster: Smooth, glabrous; dull sheen. Color: Close to 147B to 147C with faint stippling, streaks and tessellations of close to 200A; distally, close to 146B to 146C and 147B with faint stippling and streaks of close to 200A tinged with 147B.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'CRM OF14-219' as illustrated and described.

* * * * *